United States Patent [19]

Daróczy et al.

[11] 4,440,619
[45] Apr. 3, 1984

[54] ELECTRO-ANALYTICAL MEASURING EQUIPMENT WITH MEASURING CELL, COMPRISING INTEGRAL SENSING ELEMENT AND SEVERAL REFERENCE ELECTRODES

[75] Inventors: Janos Daróczy; János Erdélyi; Jenő Havas; Lajos Kecskes; Henrik Müller; Katalin Nyiró; Ferenc Takács, all of Budapest, Hungary

[73] Assignee: Radelkis Elektrokemiai Müszergyarto Szövetkezet, Budapest, Hungary

[21] Appl. No.: 353,289

[22] Filed: Mar. 1, 1982

[30] Foreign Application Priority Data

Mar. 13, 1981 [HU] Hungary .................................. 639/81

[51] Int. Cl.³ ........................................... G01N 27/28
[52] U.S. Cl. .................................... 204/401; 204/406; 204/411
[58] Field of Search ........... 204/195 R, 195 P, 195 G, 204/195 M, 195 B, 401, 406, 411; 324/425, 438; 364/499, 571

[56] References Cited

U.S. PATENT DOCUMENTS 3,539,455 11/1970 Clark .................................. 204/1 T
3,838,034 9/1974 Groves ............................ 204/195 B

*Primary Examiner*—G. L. Kaplan
*Attorney, Agent, or Firm*—Gabriel P. Katona

[57] ABSTRACT

The present invention relates to electro-analytical measuring equipment for the determination—by means of one or more measuring cells comprising sensing elements of chemical similar composition, being in constant galvanic contact with each other—of the concentration and ion-activity of solutions or of the partial pressure of gases. The sensing elements are in contact with sample or with one or more standardizing media separated in time or space. At least two reference electrodes are in direct or in indirect contact—through electrolite—with sample and standardizing medium. The reference electrodes join, in a given case, to electronic signal processor comprising arithmetic unit calculating, by fault compensation, value of one or more parameters to be measured.

5 Claims, 3 Drawing Figures

ELECTRO-ANALYTICAL MEASURING EQUIPMENT WITH MEASURING CELL, COMPRISING INTEGRAL SENSING ELEMENT AND SEVERAL REFERENCE ELECTRODES

BACKGROUND OF THE INVENTION

The present invention refers to electro-analytical measuring equipment for the selective, rapid and high-precision determination of the concentration and the ion-activity of stationary or flowing solutions or of the partial pressure of gases.

It is well known that the size of a measuring signal, e.g. membrane potential, arising on an electro-analytical sensing element of traditional construction, e.g. anion-selective membrane, is determined not only by the electrochemical parameter, e.g. ion-concentration, of the sample to be analyzed, but it is also affected by the quality, the geometrical construction and the extent of the incidental impurity of the material of the sensing element; even more, by its life, reckoned from the date of production, etc. as well. Consequently, the measuring signal arising in the course of measurement appears as the resultant of all the above listed facts. Thus, it is clear from the above that the change of the measuring signal resulting from the change of the electrochemical parameter to be measured, e.g. from the increase or the decrease of the ion-concentration, cannot be distinguished from the effect of the change of a disturbing character in the material or the condition of the sensing element.

Obviously, traditional measuring technique, calibration, standard addition, setting of the constant ion-intensity, programming of slope, etc., see e.g. Havas: Ion and molecule selective electrodes in biological systems. Latest results of chemistry, published by: Akadèmiai Kiadò in 1980, pages 80 to 87, does not strive, since it cannot strive to determine the extent of the fault-signal resulting from the disturbances already mentioned. All things considered, the methods known till now may be attributed to the comparison of the relevant electrochemical parameters of the sample and of one or more liquids, standard-solution or gas, of a known composition. It means that before the measurement is carried out, the electronic behavior of the measuring equipment and the electrochemical behavior of the measuring cell are to be harmonized (this is called: matching).

As a consequence of the uncontrollable irregularity of the disturbances occurring, the accuracy of the measurements depends obviously on the frequency of the above matching or matchings. In precision measurements it is required to carry out some matching prior to each and every measurement (at least for the sake of control). If the time necessary for the indispensable flushing of the measuring cell is also considered, the total period of the analysis will be (in the case where two standard liquids are applied) approximately five times more than the actual period of the measurements. Though by "one-spot" matching wide spread in electro-analytics this period may be reduced to one half, there is a fault resulting from the interim change of the response-function slope of the measuring cell that cannot be eliminated.

It is obvious from the above that the total period of the precision analyses is considerably long (because of the matching steps between factual measurements). On the other hand, it is impossible to carry out continuous, and at the same time high-precision measurements, as the construction of traditional measuring cells does not facilitate the determination of the fault signals during measurement, not speaking of matching to be performed simultaneously with the measurement.

SUMMARY OF THE INVENTION

The construction of the measuring equipment according to the present invention is based on the idea that the change of the parameters characteristic of the unique features of the sensing element placed in a measuring cell, e.g. standard-potential, response-function slope, can be traced even in the course of the measurement (thus it can be compensated as well) by placing in the measuring cell (over and above the sensing element in contact with the sample) one or more sensing elements of chemically similar composition, being in galvanic contact with the same, which is/are in contact with at least two standardizing media, preferably standard-solutions separated in time or space. Such sensing element is called an integral sensing element, due to its integral construction and multi-function character. Within the cell, this is connected to at least two reference electrodes in contact generally with the sample or with the standardizing media through internal electrolyte, joining the electronic signal processor.

To eliminate incidental disturbances resulting from the slightly differing electrochemical behavior of the sensing elements, despite their similar chemical composition, preferably the sensing elements (or at least two of them) are composed of one, chemically homogeneous body, i.e. the galvanic contact between the sensing elements is ensured by the material of the sensing element itself.

The continuous or intermittently continuous flowing of one or more of the standardizing media serves to eliminate the disturbing effect of the flowing potentials arising in the course of continuous or intermittently continuous measurements.

A further preferable embodiment in which the composition of the reference electrodes, standard solution and the internal electrolytes between the standard solutions and/or the sample is the same or nearly the same as the composition of the standard-solution and the sample in contact with them, aims at eliminating the disturbing effect of the diffusion potentials.

Further, the invention is based on the recognition that several measuring cells comprising integral sensing elements may be assembled so that they are in galvanic contact with each other through the sample and that their reference electrode in contact with the sample is common and thus several electrochemical parameters, e.g. the concentration of various ions, of the sample can be simultaneously determined.

Finally, in an embodiment aiming at automatization, the signal processor of the measuring equipment calculates, by fault compensation, the numerical value of one or more parameters to be measured, by analog and/or digital means, preferably by a built-in algorithm, by the application of measuring signals arising on one or more measuring cells.

The electro-analytical measuring equipment comprising a measuring cell including integral sensing elements and several reference electrodes according to the present invention is illustrated by the below described drawings and examples, without limiting the patent claims to those described above.

DETAILED DESCRIPTION OF THE INVENTION

Figure 1:
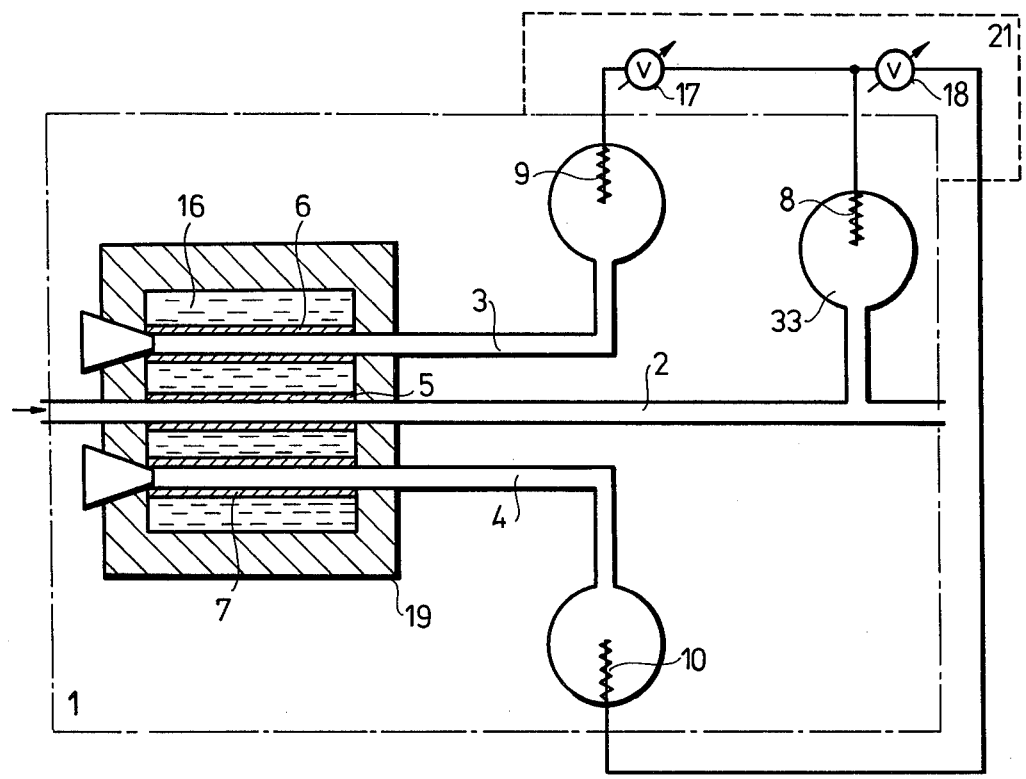
FIG. 1 is a schematic representation of the measuring equipment according to the present invention.

FIG. 1 illustrates measuring equipment with a measuring cell comprising an integral sensing element and three reference electrodes, serving for the measurement of pH.

According to the figure, in measuring cell 1, microcapillary sensing element 5 made in pH-sensitive glass is in contact, through sample 2, with internal electrolyte 33 of sample-side reference electrode 8. Similarly, in measuring cell 1, sensing element 6 having completely the same construction as sensing element 5 is connected to first standard-side reference electrode 9 through first pH standard-solution 3. The connection of sensing element 7 to second-side reference electrode 10 through second pH standard-solution 4 is completely the same as above. Electrolyte 16 ensures galvanic contact between microcapillary sensing elements 5, 6 and 7 made of pH-sensitive glass placed in cell 1. Sensing elements 5, 6 and 7 and electrolyte 16 constitute integral sensing unit 19. Electronic signal processor 21 is connected to reference electrodes 8, 9 and 10 or measuring cell 1 in such way that its measuring circle 17 is connected to first standard-side and sample-side reference electrodes 9 and 8, while its second measuring circle 18 is connected to second standard-side and sample-side reference electrodes 10 and 8.

Figure 2:
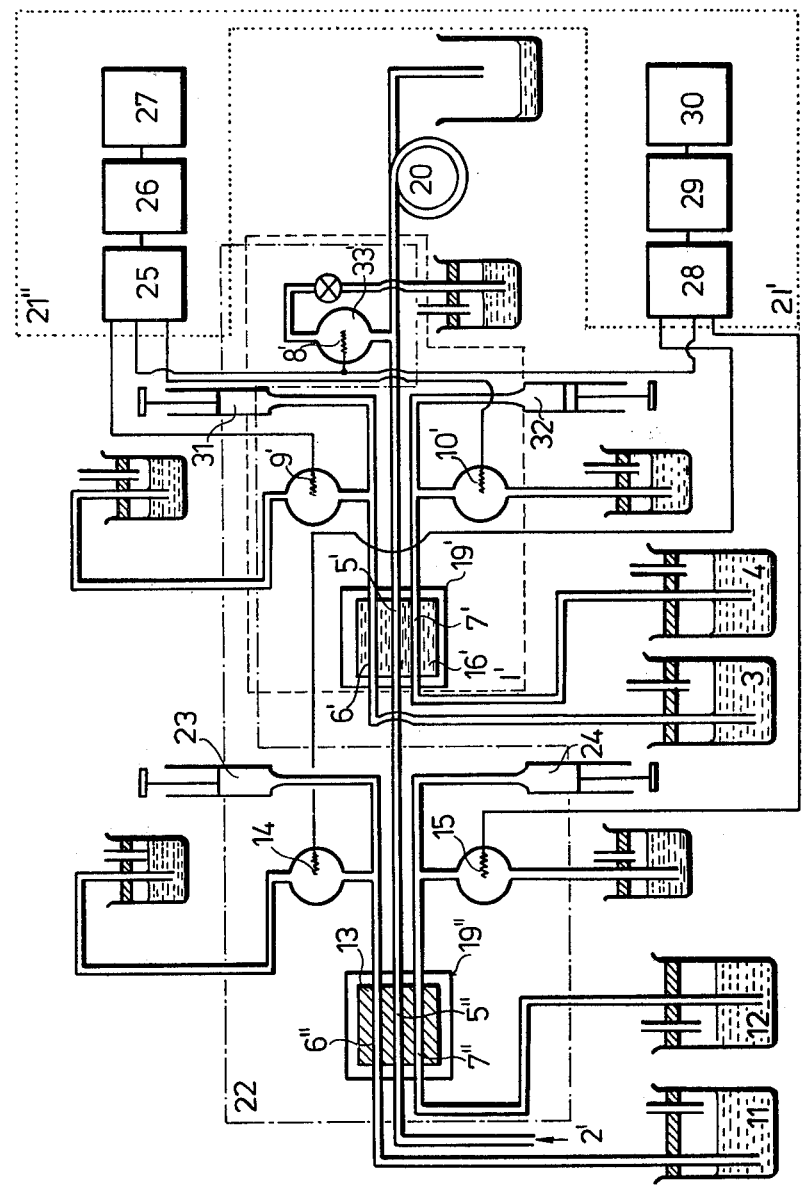
FIG. 2 is a schematic representation of another embodiment of measuring equipment according to the present invention.

FIG. 2 shows measuring equipment with a measuring cell comprising Na+ — and K+ ion-sensitive integral sensing elements and reference electrodes, in galvanic contact with each other, through the sample and having common sample-side reference electrodes.

According to FIG. 2, the construction of the Na+ ion-sensitive measuring cell 1' is the same as that of measuring cell 1 shown in FIG. 1, the only difference is that microcapillary sensing elements 5', 6' and 7', in electrolyte 16' constituting integral unit 19', are made not of pH, but of Na+ ion-sensitive glass and the first standard-solution 3' and second standard-solution 4' are not pH, but pHa standards.

The measuring equipment according to FIG. 2 comprises, besides Na+ ion-sensitive measuring cell 1', another K+ ion-sensitive measuring cell 22 as well, whose sample-side reference electrode 8' is similar to sample-side reference electrode 8 of measuring cell 1. In measuring cell 22 three microcapillary sensing elements 5", 6" and 7", in contact with sample 2', first K+ standard-solution 11 and second K+ standard-solution 12 are composed from one single, sensing body 13 of chemically homogeneous construction. Sensing body 13 constitutes, together with sensing elements 5", 6" and 7", integral sensing unit 19". In K+ ion-sensitive measuring cell 22, first K+ standard-side reference electrode 14 is also in contact with first K+ standard solution 11 and similarly, second K+ standard-side reference electrode 15 is in contact with second K+ standard-solution 12.

Na+ ion-sensitive measuring cell 1' is connected—through sample-side reference electrode 8', as well as standard-side reference electrodes 9', 10'—to the input of Na+ amplifier 25 of electronic signal processor 21", whose output joins Na+ display unit 27 through Na+ arithmetical unit 26.

Similarly, K+ ion-sensitive measuring cell 22 is connected to the input of K+ measuring amplifier 28 of electronic signal processor 21' through common sample-side reference electrode 8', as well as K+ standard-side reference electrodes 14, 15, and whose output is connected with K+ standard unit 30 through K+ arithmetical unit 29.

Besides the above, sample 2 is in contact with peristaltic pump 20, while standard-solutions 11, 12, 3' and 4' are in contact generally with liquid forwarding means 23, 24, 31 and 32.

The measuring equipment shown in FIG. 1 functions as follows:

Sensing elements 5, 6 and 7 of pH-sensitive measuring cell 1 are practically equipotential, as electrolyte 16 establishes galvanic contact between them and no current flows through them. The chemical and mechanical construction and condition of sensing elements 5, 6, 7 are completely the same. Consequently, the standard-potential arising on them, and the response-function slope characteristic of their sensitivity, are also identical. Therefore, if the electromotive force is measured between sample-side reference electrode 8 and two standard-side reference electrodes 9, 10—selected at discretion—it is practically independent from the standard potential arising on sensing elements 5, 6, 7 and obviously from their undesirable changes as well. The extent of the electromotive force to be measured between standard-side reference electrodes 9, 10 involves—even in the case of 2 sample of discretionary pH—the information of the response-function slope characteristic of the sensitivity of sensing elements 5, 6, 7, supposing the pH values of first pH standard-solution 3 and of second pH standard-solution 4 are different. Accordingly, the pH of the sample can be calculated from the value of any of the two electromotive forces measured between reference electrodes 8, 9, 10 of measuring cell 1 in such way that its value does not depend either on the standard-potential arising on sensing elements 5, 6, 7, or on the factual value of the response-function slope characteristic of their sensitivity, i.e. on their incidental meantime change causing a measuring fault.

Figure 3:
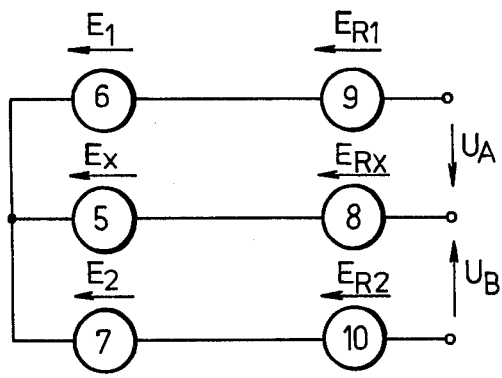
FIG. 3 is a schematic of an equivalent circuit of FIG. 1.

FIG. 3 facilitates the comprehension of the formula serving to calculate the detected pH value showing the simplified electric scheme of measuring cell 1 illustrated in FIG. 1. The formula is to determine the pH value of the sample in cases when according to FIG. 1, two potentials $U_A$, $U_B$ between sample-side reference electrode 8 and first standard-side reference electrode 9, and between sample-side reference electrode 8 and second standard-side reference electrode 8, respectively, are measured and the pH value is calculated from these values according to the following:

$$pH_x = \frac{pH_1(U_{Bx} - U_{B2}) - pH_2(U_{Ax} - U_{A1})}{(U_{Bx} - U_{B2}) - (U_{Ax} - U_{A1})}$$

in which $pH_x$ is the wanted pH-value of sample 2.

$pH_1$ is the pH-value of first standard-solution 3.

$pH_2$ is the pH-value of second pH standard-solution 4.

$U_{Ax}$ is the potential to be measured between sample-side and first standard-side reference electrodes 8, 9 if sensing element 5 is charged with sample 2.

$U_{Bx}$ is the potential to be measured between sample-side and second standard-side reference electrodes 8, 10 if sensing element 5 is charged with sample 2.

$U_{A1}$ is the potential measured when "matching" between sample-side and first standard-side reference electrodes 8, 9 if sensing element 5 is charged with first pH standard-solution 3.

$U_{B2}$ is the potential measured when "matching" between sample-side and second standard-side reference electrodes 8, 10 if sensing element 5 is charged with second pH standard-solution 4.

It appears from the formula that the required frequency of matching is determined not by sensing elements 5, 6, 7 but only by reference electrodes 8, 9, 10, i.e. by the stability of reference-potentials arising on them.

The measuring equipment illustrated in FIG. 2 operates as follows:

Na+ ion-sensitive measuring cell 1' and K+ ion-sensitive measuring cell 22 are also constructed in such way that when measuring each 2 potentials ($U_{Ax}$; $U_{Bx}$) on them according to FIG. 3, the pHA and pK value of sample 2' can be calculated according to the above formula. The obtained result factually does not depend on either the actual value of the standard-potential of the sensing elements or on that of the response-function slope, consequently, on their interim change causing a measuring fault.

Sensing body 13 does not contain electrolyte solution as galvanic contact between sensing elements 5'', 6'', 7'' is ensured by its own material.

The measuring equipment shown in FIG. 2 is more than the simple doubling of the measuring equipment with measuring cell comprising integral sensing elements according to FIG. 1.

Peristaltic pump 20 enables the application of continuous measuring technique by flowing the sample. The disturbing effect of flowing potentials arising meanwhile can be eliminated by moving standard-solution 3', 4', 11, 12 by liquid forwarding means 23, 24, 31, 32 nearly similarly to the speed of flow of the sample.

In the outlined example the disturbing effect of the diffusion potentials was eliminated in such way that standard-solutions 3', 4', 11, 12 are used as the internal electrolytes of reference electrodes 9', 10', 14, 15, while the composition of internal electrolyte 33' of sample-side reference electrode 8' is similar to the average composition of the samples to be measured.

In the measuring equipment according to FIG. 2 it is not the operator's task to calculate the wanted values characteristic of the sample, from the value of the measured potentials according to the given formula; such values are calculated by Na+ and K+ arithmetic units 26, 29 by applying $U_{A1}$ and $U_{B2}$ values measured when matching and stored. A further obvious possibility is that not only the pNa and the pK values are calculated by the arithmetic units, but directly the concentrations as well:

$$c_x = \exp_{10} \frac{\lg c_1(U_{Bx} - U_{B2}) - \lg c_2(U_{Ax} - U_{A1})}{(U_{Bx} - U_{B2}) - (U_{Ax} - U_{A1})}$$

The main advantages of the measuring equipment according to the present invention may be summarized as follows:

it enables control of the electrochemical parameters of the sensing element *during the measurement;* it enables matching *in the course of measurement;* its application makes the result of the measurement indepedent from the errors resulting from the disturbing changes in the electrochemical parameters of the sensing element;

it enables the elimination of the error resulting from the flowing potential;

its application may decrease—to a great extent—the disturbing effect of diffusion potentials;

it enables continuous or intermittently continuous measurements with considerably higher accuracy than up to now; and it may decrease considerably the total period required for the analysis.

We claim:

1. In electro-analytical measuring equipment having at least one measuring cell and an electronic signal processor for selective and rapid determination of the concentration and ion-activity of a stationary or flowing sample solution or of the partial pressure of a sample, the improvement wherein the measuring cell comprises an integral sensor having three sensing elements of chemically similar composition and in constant electrically conductive contact with each other, one of the sensing elements in contact with a sample and the other sensing elements in contact with two different standardizing media and three reference electrodes connected to the electronic signal processor, with one of the reference electrodes in contact with the sample through an internal electrolyte and the other reference electrodes in contact with the standardizing media through two other internal electrolytes.

2. The measuring equipment according to claim 1, wherein the integral sensor sensing elements are formed from one single chemically homogeneous body.

3. The measuring equipment according to claim 1 or 2, further comprising means for effecting continuous or intermittently continuous flow of at least one of the standardizing media.

4. The measuring equipment according to claim 1, comprising at least two measuring cells in electrically conductive contact with each other through the sample and having a common reference electrode in contact with the sample.

5. The measuring equipment according to claim 1, wherein the electronic signal processor comprises an arithmetical unit for calculating, by fault compensation, the value of at least one parameter to be measured.

* * * * *